United States Patent [19]
Townsend et al.

[11] Patent Number: 6,004,256
[45] Date of Patent: *Dec. 21, 1999

[54] CATALYTIC DISTILLATION OLIGOMERIZATION OF VINYL MONOMERS TO MAKE POLYMERIZABLE VINYL MONOMER OLIGOMERS USES THEREOF AND METHODS FOR SAME

[76] Inventors: Phillip Townsend, 6414 Fawnwood Dr., Spring, Tex. 77389; Aaron T. Doughty, 9930 Winchester Village Ct., Houston, Tex. 77064

[*] Notice: This patent issued on a continued prosecution application filed under 37 CFR 1.53(d), and is subject to the twenty year patent term provisions of 35 U.S.C. 154(a)(2).

[21] Appl. No.: 08/451,997

[22] Filed: May 26, 1995

[51] Int. Cl.⁶ ..................................... C07C 2/02
[52] U.S. Cl. ..................... 587/517; 508/503; 508/507; 508/508; 508/510
[58] Field of Search .................... 585/315, 503, 585/507, 508, 510, 517

[56] References Cited

U.S. PATENT DOCUMENTS

| | | | |
|---|---|---|---|
| 2,559,984 | 7/1951 | Montgomery et al. | 260/683.15 |
| 2,937,129 | 5/1960 | Garwood | 208/18 |
| 3,149,178 | 9/1964 | Hamilton et al. | 260/683 |
| 3,382,291 | 5/1968 | Brennan | 260/683 |
| 3,758,627 | 9/1973 | Juguin et al. | 260/683.15 |
| 3,763,244 | 10/1973 | Shubkin | 260/683.15 |
| 3,769,363 | 10/1973 | Brennan | 260/683.15 |
| 3,780,128 | 12/1973 | Shubkin | 260/683.9 |
| 3,876,720 | 4/1975 | Heilman et al. | 260/677 R |
| 3,997,621 | 12/1976 | Brennan | 260/677 R |
| 4,045,507 | 8/1977 | Cupples et al. | 260/638.15 |
| 4,045,508 | 8/1977 | Cupples et al. | 260/638.15 |
| 4,215,011 | 7/1980 | Smith, Jr. | 252/426 |
| 4,239,930 | 12/1980 | Allphin et al. | 585/517 |
| 4,242,530 | 12/1980 | Smith, Jr. | 585/510 |
| 4,307,254 | 12/1981 | Smith, Jr. | 568/697 |
| 4,308,414 | 12/1981 | Madgavkar et al. | 585/525 |
| 4,336,407 | 6/1982 | Smith, Jr. et al. | 568/672 |
| 4,365,105 | 12/1982 | Bercik et al. | 568/672 |
| 4,409,415 | 10/1983 | Morganson et al. | 585/525 |
| 4,429,177 | 1/1984 | Bercik et al. | 585/525 |
| 4,436,947 | 3/1984 | Morganson et al. | 585/525 |
| 4,439,350 | 3/1984 | Jones, Jr. | 252/426 |
| 4,479,023 | 10/1984 | Englehard et al. | 585/312 |
| 4,587,368 | 5/1986 | Pratt | 585/18 |
| 4,709,115 | 11/1987 | Jung et al. | 585/643 |
| 4,827,064 | 5/1989 | Wu et al. | 585/15 |
| 4,827,073 | 5/1989 | Wu et al. | 585/530 |
| 4,906,798 | 3/1990 | Lin | 585/18 |
| 4,929,788 | 5/1990 | Huang et al. | 585/522 |
| 4,935,577 | 6/1990 | Huss, Jr. et al. | 585/726 |
| 4,950,822 | 8/1990 | Dileo et al. | 585/310 |
| 4,962,249 | 10/1990 | Chen et al. | 585/329 |
| 5,019,669 | 5/1991 | Adams et al. | 585/446 |
| 5,068,487 | 11/1991 | Theriot | 585/570 |
| 5,118,872 | 6/1992 | Smith, Jr. et al. | 568/697 |
| 5,134,242 | 7/1992 | Le Quang | 585/533 |
| 5,171,909 | 12/1992 | Marquis et al. | 585/255 |
| 5,191,130 | 3/1993 | Knifton et al. | 585/255 |

OTHER PUBLICATIONS

Madgavkar, A.M. and Swift, H.E. "Fixed–Bed Catalytic Process to Produce Synthetic Lubricants From Decene–1," Ind. Eng. Chem. Prod. Res. Dev., 1983, vol. 22, pp. 675–680.

*Primary Examiner*—Helane Myers
*Attorney, Agent, or Firm*—J. M. (Mark) Gilbreth; Robert W. Strozier; Gilbreth & Strozier, P.C.

[57] ABSTRACT

This invention discloses a process for making polymerizable and/or reactable vinyl monomer oligomers with narrow molecular weight distributions using catalytic distillation and a catalyst situated in an immobile catalyst bed in a reaction zone of the distillation column reactor. The polymerizable oligomer products comprise at least 50% by weight of a single molecular weight oligomer fraction.

15 Claims, 1 Drawing Sheet

CATALYTIC DISTILLATION OLIGOMERIZATION OF VINYL MONOMERS TO MAKE POLYMERIZABLE VINYL MONOMER OLIGOMERS USES THEREOF AND METHODS FOR SAME

FIELD OF THE INVENTION

The present invention relates to a process for oligomerizing vinyl monomers as defined below, to a given level of oligomerization using a distillation column reactor containing a locationally immobile catalyst by adjusting the temperature and pressure of the column reactor to tune the process to the production of a high purity, narrowly distributed, oligomeric product for use as a polymerizable oligomer, including tactiospecific oligomers for monomers having three or more carbon atoms. Product oligomers are also useful in numerous applications which require alpha olefins or substituted alpha olefins as raw materials.

BACKGROUND OF THE INVENTION

Efforts to improve upon the various performance properties, including impact resistance, tear resistance and heat sealability among others, as well as the processability of vinyl polymers, including polyalphaolefins (PAOs), are the subject of important research and development. This research has grown especially active with the advent of tactiospecific polypropylenes and other vinyl polymers, using tactioselective catalyst such as metallocene catalysts. Although many of these new, sophisticated plastics have good thermal stability and strength, they tend to be brittle and have inferior impact resistance to other plastic products. Efforts to improve the impact resistance of PAOs have recently centered around polymer blends or post polymerization treatments.

Efforts have also been directed at improving the performance properties and processability of crystalline vinyl polymers such as tactiospecific polyalphaolefins polymers by introducing 1-alkene co-monomers with longer alkyl chains into the molecule as side chains to disrupt the crystal packing efficiency of the crystalline vinyl polymers. Efforts have also been directed at decreasing the tactiospecificity of the resulting vinyl polymer or PAO to find a compromise between strength, heat resistance and impact strength.

Due largely to studies on the polymerization of propene, 1-decene and other vinyl monomers, the mechanism of the polymerization of 1-alkene and the effect of that mechanism on polymer structure is reasonably well understood, providing a strong resource for targeting potentially useful oligomerization methods and oligomer structures.

The present invention takes advantage of the ability to combine a chemical transformation and/or reaction and a product separation using a distillation column reactor (DCR). This technique has been called catalytic distillation. Continuous removal of a desired product from the DCR provide one of the unique features that gives catalytic distillation its technical and economic advantages such as lower energy requirements, higher yields, improved product purity, and lower capital investment.

A DCR is generally a conventional fractionation tower equipped with an overhead condenser, reflux pump, reboiler, and control instrumentation, but additionally equipped or fitted with a reaction zone, containing a catalyst, where reaction and distillation occur simultaneously. Depending upon boiling points, feed components are introduced above or below the catalyst zone or bed. Products, unreacted monomers, and other components are continuously removed from the reaction zone by the distillation process.

Catalytic distillation is suitable only for chemical reactions where the distillation of reaction components occurs in the same temperature and pressure range as the reaction. Thus, operation above the critical point can be a limitation, and the presence of azeotropes or close boiling components may cause difficulties.

The catalyst must be stable and insoluble in the feeds or products. The catalyst should be relatively immune to poisoning because frequent catalyst replacement can be costly. The particular catalyst, which generally is a solid material, can include catalyst coated monoliths, catalyst coated packings, or various types of pocketed catalyst packings.

In operation, the reaction liquid and vapor should be able to freely flow through the catalyst zone without unacceptable pressure hindrance and should be able to come to sufficient contact with catalytically active surface, sites, or regions to ensure that the desired chemical transformation occurs in the reaction zone. Also, the method of catalyst packing should be designed to prevent by-passing. The total bed height, or reaction zone, and its position in the DCR are determined by the feed type and composition, and the products and purity desired.

Generally, the chemical transformation and/or reaction occurs in the liquid phase in the presence of a solid catalyst. However, certain gas phase chemical transformation and/or reaction can also occur at the catalyst surface, especially when the reaction zone temperature is tuned to an intermediate molecular weight product. The desired product, having higher molecular weight and generally a higher boiling point than undesirable, lower molecular weight monomers or products, is then fractionally separated into the bottom portion of the DCR upon leaving the reaction zone.

Catalytic distillation has been used commercially to produce a variety of important chemicals including: methyl tert-butyl ether as described in W. Stadig, Catalytic Distillation, Chemical Processing (February, 1987), U.S. Pat. Nos. 4,232,177 and 4,307,254; cumene by alkylating propylene with benzene as described in J. Shoemaker et al., "Cumene by Catalytic Distillation," Hydrocarbon Processing, p. 57 (June, 1987); synthetic polyalphaolefin (PAO) lubricants using a DCR to keep a volatile catalyst in the DCR to accomplish the oligomerization as described in U.S. Pat. No. 4,907,798; alkylation of aromatic compounds using cationic exchange resin including those containing sulfonic acid groups, naturally occurring zeolites and synthetic zeolites as described in European Pat. Application No. 189,683; and heterogeneous isoparaffin/olefin alkylation and oligomerization of alpha olefins using a composite catalyst comprising a Lewis acid promoted non-zeolite solid inorganic oxide, large pore crystalline molecular sieve and/or ion exchange resins in the presence of water as described in U.S. Pat. No. 4,935,577. Similar, non-DCR processes are described in U.S. Pat. No. 4,384,161, 3,855,342 and 3,862,258.

The catalytic distillation technique has also been used for various chemical separations and transformations including: separating isobutene from a mixture comprising n-butene and isobutene as described in U.S. Pat. Nos. 4,242,530 and 4,215,011 using sulfonic acid modified ion exchange resins; and transetherification as described in U.S. Pat. No. 4,510,336, relates to carried out in a catalytic distillation reactor.

The preceding references are incorporated by reference.

Thus, it would be a substantial advancement in the art to be able to prepare oligomeric products of vinyl monomers with narrow molecular weight distributions for use as polymerizable monomers to improve the performance properties, including impact resistance, and processability of polymers made from the same or different vinyl monomers. Additionally, such oligomers would represent new raw materials for various chemicals heretofor made from alpha olefins, including those with from 6 to 30 carbon atoms.

SUMMARY OF THE INVENTION

Figure 1:
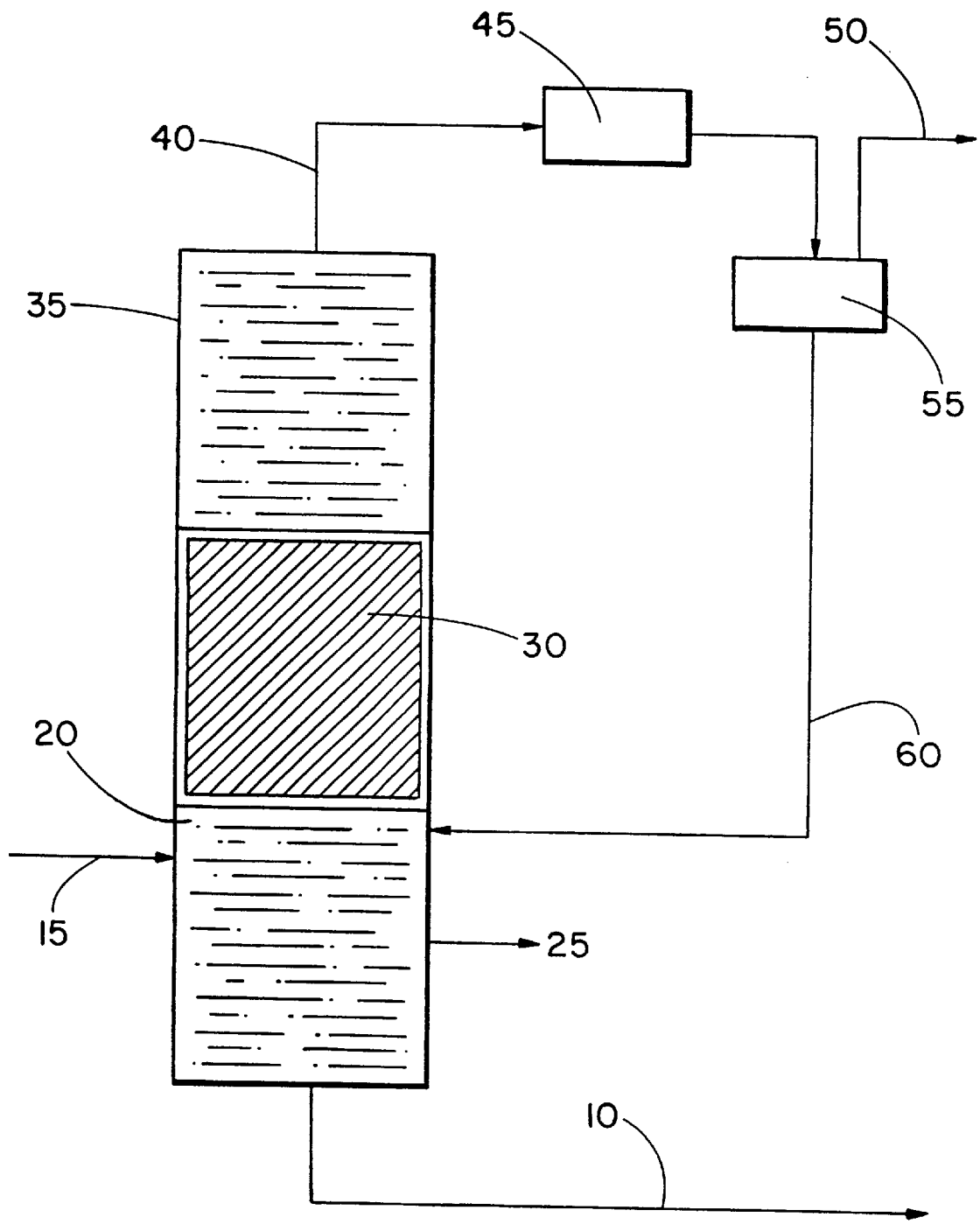
FIG. 1 is a schematic representation of a DCR flow diagram useful for preparing the oligomers of the present invention.

The present invention provides a process for oligomerizing vinyl monomers, as defined below, having between 2 and about 30 carbon atoms by contacting one or more vinyl monomers with a locationally immobile catalyst in a distillation column reactor (DCR). The DCR temperature and pressure is controlled to be sufficient: (1) to maintain, in a reactive zone of the DCR, a reactive oligomer fraction; (2) to allow a lower boiling oligomer fraction and the monomers to fractionate and be taken overhead together with inert or non-reactive feed components into a top zone of the DCR for possible recycle or rejection of light ends; (3) to maintain suitable temperature and pressure in the catalytic zone; and (4) to allow a desired oligomer fraction to fractionate and migrate to a bottom zone of the DCR for removal as the oligomerization proceeds.

The present invention also provides an oligomerization process comprising:
  (a) feeding one or more vinyl monomers having between 2 and about 30 carbon atoms to a DCR into a feed zone;
  (b) concurrently in the DCR;
    (i) contacting the vinyl monomers with an immobile catalyst localized in a catalyst bed in a reaction zone of the DCR; and
    (ii) simultaneously fractionating the monomers, a reactive oligomer fraction, and a product or desired oligomer fraction together with non-reactive feed components and a low boiling oligomer fraction;
  (c) withdrawing the desired oligomer fraction from a bottom zone of the DCR below the feed zone; and
  (d) withdrawing unreacted monomer and the non-reactive feed components along with the low boiling oligomers or low boiling reaction by-products from a top zone of the DCR above the feed zone.

The present invention also provides a oligomer product comprising a narrow molecular weight distributed, polymerizable oligomer of one or more vinyl monomers having between about 2 to about 30 carbon atoms where the molecular weight distribution of the oligomer product comprises at least 50% of an oligomer fraction having a given number of monomer units.

The present invention also provides a method for making higher performance, including more impact resistance, and more processable polymers by contacting one or more C2 to about C30 vinyl monomers and a narrow molecular weight distributed, polymerizable oligomer of the same monomers with a polymerization catalyst where the polymerizable oligomers produce periodic side chains in the main polymer chain. These periodic side chains cause periodic disruptions in the packing efficient of the polymers resulting in improved impact resistance.

The present invention further provides impact resistant polymers including periodic oligomeric side chains in a main chain of the polymer, where the side chains are designed to disrupt the packing efficiency of the polymer and thereby improve the impact resistance to the polymer.

DETAILED DESCRIPTION OF THE INVENTION

The inventors have discovered that narrow molecular weight distributed, polymerizable vinyl monomer oligomers can be prepared without the necessity of resorting to a separate distillation step to narrow the molecular weight distribution of the oligomer. By the present invention, oligomers of one or more vinyl monomers including alpha-olefins of 1-alkene monomers, are made which have physical properties similar to oligomer products comprising a majority (>50%) of a single molecular weight oligomer product, i.e., a given degree of oligomerization.

Likewise, the polymerizable oligomer of the present invention can be used to functionalize other organic molecules including vinyl bonds. Such functionalizations can result in a wide variety of alpha olefin derivatives and derivatives of other organic molecules such as aromatics. Examples of these numerous derivatives include detergents, plasticizers, lubricants, solvents, and the like.

The process of the present invention is ideally suited for preparing narrow molecular weight distributed oligomers of alpha olefins (1-alkenes) to be used a polymerizable monomers to disrupt the crystal structure of polyalphaolefins (PAOs) including polyethylene, polypropylene and others, and thereby improve the impact resistance, other performance properties and processability of PAOs. This process is particularly useful in preparing tactiospecific alpha olefin oligomers to improve the impact resistance to tactiospecific PAOs.

The invention comprises the steps of vinyl monomer oligomerization to produce narrow molecular weight distributed, polymerizable vinyl monomer oligomers. This process is comprised of catalytic distillation in the presence of a locationally immobile catalyst.

Catalytic distillation employs a catalytic distillation column which is generally a standard column with at least three zones so as to separate the product from the rest of the process and feeds. More zones may be desirable to separate other products or feed components. This column must have the ability to be packed with standard distillation packing and with an immobile catalyst in a localized catalyst bed in the DCR. This column may need to be run under vacuum to lower the boiling temperatures of the monomer feed and/or the oligomers. The desired temperature to achieve commercial productivity is the highest temperature that can be tolerated by the oligomer product in the column bottom as well as the highest bed temperature which can be tolerated by the catalyst.

The amount of vacuum or pressure required will vary with the starting monomer composition and the desired product. For example, if the desired product is an oligomer of propylene comprising at least 50 wt. % of an oligomer having 20 propylene units, then the pressure need not be reduced as low as would be required if the desired product is centered around an oligomer having 30 propylene units.

The bottom zone will be run at a temperature so as to boil the vinyl monomers and preferably the 1-alkene monomers and any lower boiling, undesired oligomer fraction into the second or middle zone thereby allowing further chain growth. This bottom zone will be the removal zone for the final desired oligomer product or fraction.

The second or middle zone will be a catalyst or reaction zone for the oligomerization reaction of the vinyl monomers. This zone pressure and temperature will be set near the boiling point of a reacting oligomer fraction. The monomer feed will ideally be fed just below the reaction zone. As the monomer feed is boiled into the reaction zone, the feed reacts with itself or with previously formed oligomer at the catalytic sites. The catalyst in this zone will be immobile either directly, packed and/or supported so as to remain fixed in the zone. The reaction zone is design to also promote simultaneous distillation (by any of the methods previously described).

The inventors have also found that for maximum control of molecular weight, the rate of association/dissociation of oligomer with the catalyst should be higher than the rate of monomer insertion into the catalyst-associated oligomers, and preferably, the rate of association/dissociation should be much higher than the rate of monomer addition to a growing oligomer chain.

The top zone and overhead will be for the recovery and recycle of unreacted monomer while rejecting any nonreactive feed components. This is an essential feature of the DCR because this recovery allows high oligomer on monomer yields. Using catalytic distillation allows the feed stream to have close-boiling contaminants as long as they do not contaminate the catalyst. For instance, if propylene is contaminated with the inert compounds, propane, this and other contaminants should be rejected by the distillation process since they will not react with the catalyst under DCR operating conditions. The overhead can also be recycled to the feed as well as refluxed.

The bottom or removal zone can consist essentially of the desired or product oligomer fraction or can consist of the desired oligomer product and a secondary bottoms component. The secondary bottoms component should have a similar boiling point to the desired product under the DCR operating conditions and should be inert under the DCR conditions. That is, the secondary bottoms component should not react with the desired product or with the catalyst.

If a secondary bottoms component is used, then the DCR will generally have a bottom fraction separation unit associated. The bottom fractionation unit is designed to remove the desired oligomer product from the secondary component and recycle the secondary component to the DCR bottom zone. In this way, the DCR can be operated above the thermal polymerization temperature of the oligomer product because the oligomer product concentration can be kept relatively low during DCR operation.

The catalyst used in the process must be capable of oligomerizing olefins and have a decomposition or de-attachment temperature which is considerably higher than the boiling point of the reacting fraction under the operating conditions. The catalyst must be immobilized in the reaction zone under the operating conditions and must also allow simultaneous distillation and product fractionation at reasonable efficiency.

By using catalytic distillation, this method will prevent monomer and lower boiling oligomers from entering the DCR bottom zone and thus, the product. In addition, since the desired oligomer (e.g., trimer of 1-decene) will rapidly fall or fractionate to the bottom zone of the DCR away from the catalyst zone as it is formed, this will greatly reduce the yield of higher oligomers that can form by further growth if the desired oligomers remain in contact with the catalyst. Thus, a tight or narrow molecular weight distribution or carbon number indexed product will occur.

The method of the present invention can be better understood by reference of FIG. 1. The method utilizes a DCR unit including a distillation column 5 having a bottom zone 25, a catalyst zone 30, and a top zone 35. The catalyst zone 30 contains a catalyst bed 31 containing an immobilized catalyst. The bottom zone 25 and the top zone 35 can include standard column packings or trays 20. To the bottom zone 25 is fed the olefin or vinyl monomer, so as to introduce feed below the catalyst zone 30. The monomer feed boils up the column 5 where it contacts the catalyst and undergoes oligomerization.

The top zone 35 includes an overhead withdrawal pipe 40 which leads into a condenser 45 where the overhead is liquified. The liquified overheads are forwarded to a separator 55 where the lights are discarded and the monomers and light oligomers are recycled to the column 5 through pipe 60.

The bottom zone 25 includes a bottom withdrawal pipe 10 through which the desired oligomer product is withdrawn from the DCR 5.

The oligomerization reaction in a fixed bed can be conveniently carried out within the broad range of liquid hourly space velocities, that is, the volume of the liquid feed per volume of catalyst per hour of about between 0.1 and about 20 hours-1; but preferably the reaction is carried out within the range of about 0.2 and about 5 hours-1.

The present invention can also be practiced using multiple DCR reactors each reactor tuned to a specific oligomer product. Thus, a vinyl monomer trimer could be made in a first DCR reactor. The trimer product would then be forwarded from the bottom zone of the first DCR reactor to the feed zone of a second DCR tuned to make hexamer or higher oligomer products. This arrangement of DCR units in series can be extended to yield a desired oligomeric product. The use of multiple DCRs provides better control over the molecular weight distribution of the product. It also provides away to form oligomeric products with bi-modal or multi-modal molecular weight distribution, i.e., the product would include several different oligomer products each with its own specific narrow molecular weight distribution.

The distillation column reactor may be operated at sub-atmospheric, atmospheric or super-atmospheric pressure. The temperature in the bed will be the boiling point of the mixture at the operating pressure. The pressure will generally range from about 15 Torr to near atmospheric with corresponding bed temperatures of about 60° F. to about 300° F., preferably from about 80 Torr to about 600 Torr and 80° F. to about 200° F.

Such conventional items as valves, reboilers, slip streams, etc. are not shown, but would be obvious expedients to setting up such equipment.

Catalysts suitable for use in the present invention include, without limitation, Lewis acid catalyst, including Friedel-Crafts type catalysts Ziegler-Natta, Ziegler, and Natta catalyst, metallocene catalysts, and the like which are capable of being immobilized in a catalyst bed or zone in a DCR. Additionally, the Lewis Acid catalyst suitable for use in the present invention include, without limitation, the catalyst disclosed in U.S. Pat. Nos. 4,827,064, incorporated herein by reference.

The catalyst suitable for the present invention should have association/disassociation rates comparable to and preferably greater than the rate of monomer insertion into a growing oligomer chain. Additionally, the rate at which the desired oligomer leaves the catalyst zone should exceed the rate at which it alternatively reassociates with the catalyst. These requirements ensure that the distillation portion of the process will have adequate time to discriminate between oligomer fractions. It is thought that the above rate relationship between monomer insertion, association/dissociation and residence time in the reactor zone are essential elements for peaking the molecular weight distribution of the desired oligomeric fraction.

Suitable Ziegler-Natta, Ziegler, and Natta catalyst include, without limitation, catalysts containing one or more group 3, 4, or 5 metals or Lu, La, Nd, or Sm. Such catalysts include, without limitation, those disclosed in following U.S. Pat. Nos. 3.305,538, 4,530,914, and 3,893,989, incorporated herein by reference.

Suitable metallocene catalyst include, without limitation, metallocene (rigid or freely rotating) containing one or more group 3, 4, or 5 metals, or Lu, La, Nd, or Sm. Such metallocene catalysts include, without limitation, those disclosed in the following U.S. Pat. Nos. 5,120,867, 5,017,714, 4,287,328, 4,794,096, 3,258,455, 3,364,190, 5,225,550, 5,225,500, 4,892,851, 5,296,434, 5,268,495, and 5,132,262, incorporated herein by reference.

Suitable supports for use with the catalyst of the present invention include without limitation, non-zeolitic solid inorganic oxides such as alumina, silica, boria, oxides of phosphorus, titanium dioxide, zirconium dioxide, chromia, zinc oxide, magnesia, calcium oxide, silica-alumina, silica-magnesia, silica-alumina-magnesia, silica-alumina-zirconia, chromia-alumina, alumina-boria, silica-zirconia, etc. and the various naturally occurring inorganic oxides of various states of purity such as bauxite, clay, diatomaeous earth etc. the preferred inorganic oxides are amorphous silicon dioxide and aluminum oxide.

The large pore crystalline molecular sieves which can be used in the present invention include those which have pores sufficiently large to physically absorb 2,2,4-trimethylpentane. Representative large pore crystalline molecular sieves include, for example the following zeolites: ZSM-3, ZSM-4, ZSM-12, ZSM-18, ZSM-20, zeolite beta, zeolite L, mordenite, faujasite, zeolite Y, and the rare earth metal-containing forms of the above. For the purposes of this invention, zeolite Y includes zeolite Y in its as synthesized form, as well as its variant forms including framework dealuminated zeolite, e.g., ultrastable Y (USY) described in U.S. Pat. No. 3,293,192 and LZ-210 described in U.S. Pat. No. 4,503,023, hereby incorporated by reference.

The large pore zeolite selected for use in the improved alkylation process of this invention generally can possess an alpha value over a wide range of from less than 1 to over 1000. "alpha value", or "alpha number", is a measure of zeolite acidic functionality and is more fully described together with details of its measurement in U.S. Pat. No. 4,016,218, J. Catalysis, 6, pp. 278–287 (1966) and J. Catalysis, 61, pp. 390–396 (1980). Zeolites of low acidity (alpha values of less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite can be exposed to steam at elevated temperatures ranging from about 500 degree(s) to about 1200 degree(s) F. and preferably from about 750° F. to about 1000° C. This treatment can be accomplished in an atmosphere of 100% steam or an atmosphere consisting of steam and a gas which is substantially inert to the zeolite. A similar treatment can be accomplished at lower temperatures using elevated pressure, e.g., at from about 350° F. to about 700° F. With from about 10 to about 200 atmospheres. Specific details of several steaming procedures may be gained from the disclosures of U.S. Pat. Nos. 4,325,994; 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Other large pore crystalline molecular sieves which can be used in the present invention include pillared silicates and/or clays; aluminophosphates, e.g., ALPO-5, VPI-5; silicoaluminophosphates, e.g., SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875 and 4,742,033.

The catalysts of the present invention can also be supported on the surface of inorganic oxide or metallic monolithic supports such as honeycombed supports, and structured packings or loose fill packings such as rings, saddles and the like.

The catalyst suitable for the present invention can be immobilized on organic supports such as polymeric resin beads including macroreticular polystyrene resin beads available from Rohm & Haas Co. or Dow Chemical and other, functionalized, high temperature polyamide resins or fabrics, functionalized polyarylimides, polyarylsulfones, polyarylsulfides and the like. The supports can even be made into woven fabric with the catalyst immobilized in the fibers making up the woven fabric. The catalysts can also be immobilized in organic liquid crystalline polymeric webbing or sheets, provided of course, that the liquid crystalline polymers do not melt, or flow or release the catalyst under DCR operating conditions. As with liquid crystal polymers, the other organic polymer supports must not melt or flow or release the catalyst under DCR operating conditions.

The catalysts of the present invention can also been placed in containers which are positioned in the catalyst bed of the DCR. The container employed to hold the catalyst particles may have any configuration, such as the pockets, cylinders, spheres, doughnuts, cubes, tubes or the like.

As is generally true with most catalysts and especially immobilized catalysts, the smaller the particle size of the catalyst and/or its support the greater the activity at constant catalyst volume, i.e., the greater the number of catalytically active sites. However, a catalyst bed formed from too finely sized particles tends to restrict the flow across the catalyst bed. For these reasons, the particle size of the catalyst is preferably a compromise between the resulting pressure drop and activity.

The vinyl monomers suitable for use in the present invention include all polymerizable vinyl monomers, but preferably, all vinyl monomers with one unsubstituted olefinic terminus, i.e., the preferred vinyl monomers are represented by formula (I):

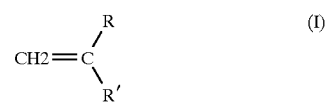

where R and R' are the same or different, and collectively having between 0 and about 28 carbon atoms. R and R' can be a hydrogen atoms, a halogen atom, a cyano group, a hydroxy group, an alkoxy group, a linear or branched alkyl group, a linear or branched halogenated alkyl group, an aryl group, a halogenated aryl group, an alka aryl group, an halogenated alka aryl group, an alka alkoxy substituted aryl group, an ara alkyl group, an halogenated ara alkyl group, other substituted alka aryl group and ara alkyl groups, a carbonyl group, a carboxylic acid group, a carboxylate ester group, an amide group, or the like. The preferred monomer of formula (I) are monomers where R' is hydrogen. Particularly, preferred monomers of formula (I) are monomers where R' is hydrogen and R is a hydrogen atom, a halogen atom, a linear C1 to about C28 alkyl group or halogenated linear C1 to C28 alkyl group, a C6 to about C28 ara alkyl group or alka aryl group or halogenated analogs thereof. Especially preferred monomers of formula (I) are monomer where R' is hydrogen and R is a hydrogen atom, a linear C4 to C18 alkyl group, i.e., C6 to C20 1-alkenes, and halogenated analogs thereof. The most preferred monomers for are C2 to C12 1-alkenes.

Exemplary vinyl monomers for use in the present invention include, without limitation:
ethylene, propylene, 1-butene, isobutylene, 1-pentene, isopentene, 1-hexene, isohexene, and similar 1-alkenes and isoalkenes; 1,1-diethylethylene, and similar 1,1 disubstituted ethylenes; acrylonitrile, methacrylonitrile, acrylic acid, methacrylic acid, acrylate and methacylates such as methylacrylate, methylmethacrylate, ethylacrylate, ethylmethacrylate, propylacrylate, propylmethacrylate, and the like; styrene, methylstyrene, alpha-methyl styrene, other alkylated styrenes, chloro and fluoro styrenes, perfluoro styrenes, methoxylated styrene, and the like; vinyl chloride, vinyl chloride, vinylidene fluoride, and the like; 3,3,3-trifluoropropene, 1-perfluoropropyl ethylene, and other perfluorinated alkyl substituted ethylenes, and other polymerizable vinyl monomers.

The vinyl monomer feed streams may be relatively pure single monomer streams, relatively pure mixed monomer streams, or streams containing a single or a mixture of vinyl monomers. Such streams can contain alkane and other higher and lower hydrocarbon components. One advantage of the present process is that relatively low concentrations of vinyl monomers may be substantially removed from mixed streams by the oligomerization process. However, pure or substantially pure single or mixed vinyl monomer streams are preferred.

The subject process is directed to preparation of an oligomerized vinyl monomer by oligomerizing one or more vinyl monomers in the presence of an immobilized catalyst to a product characterized by one more peaks in the product's molecular weight distribution (MWD). The oligomer products of the present invention will comprise one or more oligomer fractions having at least 50 wt. % of a single oligomer fraction. The single oligomer fraction is a fraction having a given degree of oligomerization, i.e., a single oligomer fraction could be an oligomer having a degree of oligomerization of 12 (twelve monomer units in the oligomer chain). Preferably, each oligomer fraction will comprise at least 55 wt. % of a single oligomer fraction. And, more particularly, each oligomer fraction will comprise at least 60 wt. % of a single oligomer fraction.

The present invention is also directed to a method for making high performance, impact resistant, processable polymers by contacting one or more C2 to about C30 vinyl monomer(s) and a narrow molecular weight distributed, polymerizable vinyl monomer oligomer with a polymerization catalyst where the oligomer is periodically incorporated into the growing polymer chain as an oligomer side chain. Preferably, the polymerizable oligomer is composed of the same monomers as the polymer and have the same tactiospecificity in the case of monomers and catalyst capable of forming tactiospecific polymers. The periodic inclusion of the oligomer side chains in the main polymer chain causes periodic disruptions in the packing efficient of the resulting polymer. Such periodic disruptions in the packing efficient results in improved impact resistance, tear resistance, processability or other polymer properties. The method used can be similar to the methods for making vinyl monomer polymers disclosed in the U.S. Pat. Nos. listed for Ziegler-Natta catalysts and metallocene catalyst.

The present invention is also directed to improved performance and impact resistant polymer including periodic oligomer side chains in a main polymer chain, where the side chains are designed to disrupt the packing efficiency of the polymer and comprise an oligomer of the present invention as described above. Preferably, the polymer and oligomer have the same monomer composition and the same microstructure.

The term microstructure refers to manner of monomer insertion in the growing oligomer and/or polymer chains. If tactiospecific catalysts are used, then the microstructure of the resulting oligomer or polymer will have a given tacticity such as isotactic, syndiotactic, hemi-isotactic, atactic, or mixtures thereof. The term is also meant to refer to the nature of the addition, i.e., head to tail, tail to head, head to head, tail to tail or mixtures thereof.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:
1. An oligomerization process comprising:
 (a) feeding one or more vinyl monomers having between 2 and about 30 carbon atoms into a feed zone of a distillation column reactor (DCR);
 (b) concurrently in the DCR:
  (i) contacting the vinyl monomers with an immobile catalyst localized in a catalyst bed in a reaction zone of the DCR where the catalyst has a rate of association/dissociation of a growing oligomer chain that is greater than the rate of monomer insertion into the growing chain; and
  (ii) simultaneously fractionating the monomers, a reactive oligomer fraction, and a product or desired oligomer fraction together with non-reactive feed components and a low boiling oligomer fraction such that the molecular weight distribution comprises at least 50% of a single molecular weight oligomer;
 (c) withdrawing the desired oligomer fraction from a bottom zone of the DCR below the feed zone; and
 (d) withdrawing unreacted monomer and the non-reactive feed components along with the low boiling oligomers or low boiling reaction by-products from a top zone of the DCR above the feed zone.
2. The process of claim 1, further comprising:
 (e) feeding the desired product of step (a) to a second DCR into a feed zone;
 (f) concurrently in the second DCR:
  (i) contacting the desired product of step (a) with an immobile catalyst localized in a catalyst bed in a reaction zone of the second DCR where the catalyst has a rate of association/dissociation of a growing oligomer chain that is greater than the rate of monomer insertion into the growing chain; and

(ii) simultaneously fractionating the desired product of step (a), a reactive oligomer fraction, and a second product or a second desired oligomer fraction together with non-reactive feed components such that the molecular weight distribution of the second desired oligomer fraction is narrowed;

(g) withdrawing the second desired oligomer fraction from a bottom zone of the second DCR below the feed zone; and (h) withdrawing unreacted desired product from step (a) and the non-reactive feed components along with any low boiling oligomers or low boiling reaction by-products from a top zone of the second DCR above the feed zone.

3. The process of claim 1, wherein the vinyl monomers are represent by formula (I)

where R and R' are the same or different, and collectively having between 0 and about 28 carbon atoms.

4. The process of claim 3, wherein R and R' are a hydrogen atom, a halogen atom, a cyano group, a hydroxy group, an alkoxy group, a linear or branched alkyl group, a linear or branched halogenated alkyl group, an aryl group, a halogenated aryl group, and alka aryl group, an halogenated alka aryl group, an alka alkoxy substituted aryl group, an ara alkyl group, an halogenated ara alkyl group, other substituted alka aryl group and ara alkyl groups, a carbonyl group, a carboxylic acid group, a carboxylate ester group, or an amide group.

5. The process of claim 3, wherein R' is hydrogen.

6. The process of claim 3, wherein R' is a hydrogen atom and R is a hydrogen atom, a halogen atom, a linear C1 to about C28 alkyl group or halogenated linear C1 to C28 alkyl group or a C6 to about C28 ara alkyl group or alka aryl group or halogenated analogs thereof.

7. The process of claim 3, wherein R' is a hydrogen atom and R is a hydrogen atom, a linear C4 to C18 alkyl group or halogenated analogs thereof.

8. The process of claim 1, wherein the vinyl monomers are C2 to C12 1-alkenes.

9. A method for making branched polymers comprising the step of contacting at least one C2 to about C30 vinyl monomers and at least one narrow molecular weight distributed, polymerizable oligomer of claim 1 with a polymerization catalyst where the polymerizable oligomers introduce periodic side chains in the polymer.

10. The method of claim 9, wherein the vinyl monomers are represent by formula (I)

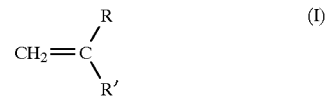

where R and R' are the same or different, and collectively having between 0 and about 28 carbon atoms.

11. The method of claim 10, wherein R and R' are a hydrogen atom, a halogen atom, a cyano group, a hydroxy group, an alkoxy group, a linear or branched alkyl group, a linear or branched halogenated alkyl group, an aryl group, a halogenated aryl group, an alka aryl group, an halogenated alka aryl group, an alka alkoxy substituted aryl group, an ara alkyl group, an halogenated ara alkyl group, other substituted alka aryl group and ara alkyl groups, a carbonyl group, a carboxylic acid group, a carboxylate ester group, or an amide group.

12. The method of claim 10, wherein R' is hydrogen.

13. The method of claim 10, wherein R' is a hydrogen atom and R is a hydrogen atom, a halogen atom, a linear C1 to about C28 alkyl group or halogenated linear C1 to C28 alkyl group or a C6 to about C28 ara alkyl group or alka aryl group or halogenated analogs thereof.

14. The method of claim 10, wherein R' is hydrogen and R is a hydrogen atom, a linear C4 to C18 alkyl group or halogenated analogs thereof.

15. The method of claim 9, wherein the vinyl monomers are C2 to C12 1-alkenes.

* * * * *